United States Patent [19]
Olsen

[11] Patent Number: 5,688,257
[45] Date of Patent: Nov. 18, 1997

[54] MENSTRUATION TAMPON AND A METHOD OF MANUFACTURING THE SAME

[75] Inventor: Clas Olsen, Vestskogen, Norway

[73] Assignee: Mölnlycke AB, Gothenburg, Sweden

[21] Appl. No.: 448,484

[22] PCT Filed: Dec. 27, 1993

[86] PCT No.: PCT/SE93/01108

§ 371 Date: Aug. 16, 1995

§ 102(e) Date: Aug. 16, 1995

[87] PCT Pub. No.: WO94/15565

PCT Pub. Date: Jul. 21, 1994

[30] Foreign Application Priority Data

Dec. 30, 1992 [SE] Sweden ................... 9203942

[51] Int. Cl.⁶ ...................................... A61F 13/15
[52] U.S. Cl. ................. 604/363; 604/904; 604/358; 28/118
[58] Field of Search ................. 604/904, 363, 604/358; 28/118, 120, 121

[56] References Cited

U.S. PATENT DOCUMENTS

| | | |
|---|---|---|
| 4,222,381 | 9/1980 | Widlund et al. ............ 604/904 |
| 4,743,237 | 5/1988 | Sweere . |
| 4,816,100 | 3/1989 | Friese ........................ 604/904 |
| 5,084,038 | 1/1992 | Sheldon et al. ............ 604/904 |
| 5,153,971 | 10/1992 | Van Iten ..................... 604/904 |
| 5,350,371 | 9/1994 | Van Iten ..................... 604/904 |
| 5,374,258 | 12/1994 | Lloyd et al. ................ 604/904 |

FOREIGN PATENT DOCUMENTS

| | | |
|---|---|---|
| 370320 | 10/1974 | Sweden . |
| 2010680 | 7/1979 | United Kingdom . |

*Primary Examiner*—Paul B. Prebilic
*Assistant Examiner*—Dennis Ruhl
*Attorney, Agent, or Firm*—Burns, Doane, Swecker & Mathis, L.L.P.

[57] ABSTRACT

A tampon (8) includes an absorbent body (2) which is embraced by a fluid-permeable casing (4) of thermoplastic non-woven material. A withdrawal string (7) attached to the absorbent body (2) exits centrally from one end surface (10) of the tampon. The casing material (4) is heat-sealed at least at the central part of the end surface (10), by pressing a mandrel (9) against the end (10) of the tampon, so as to coalesce the thermoplastic material to an essentially fluid-impervious film (11). This improves the protection of the tampon against leakage and also increases the stability of the tampon.

13 Claims, 1 Drawing Sheet

U.S. Patent
Nov. 18, 1997
5,688,257
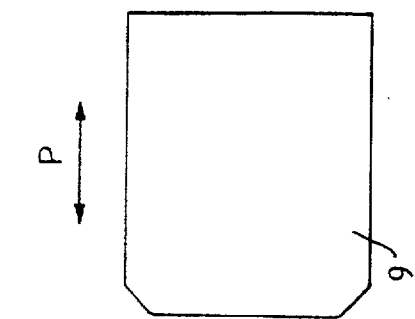
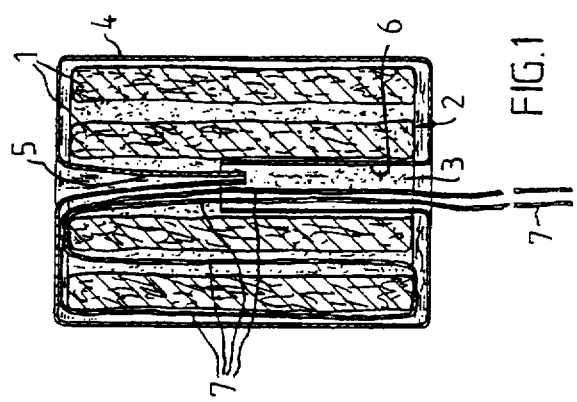
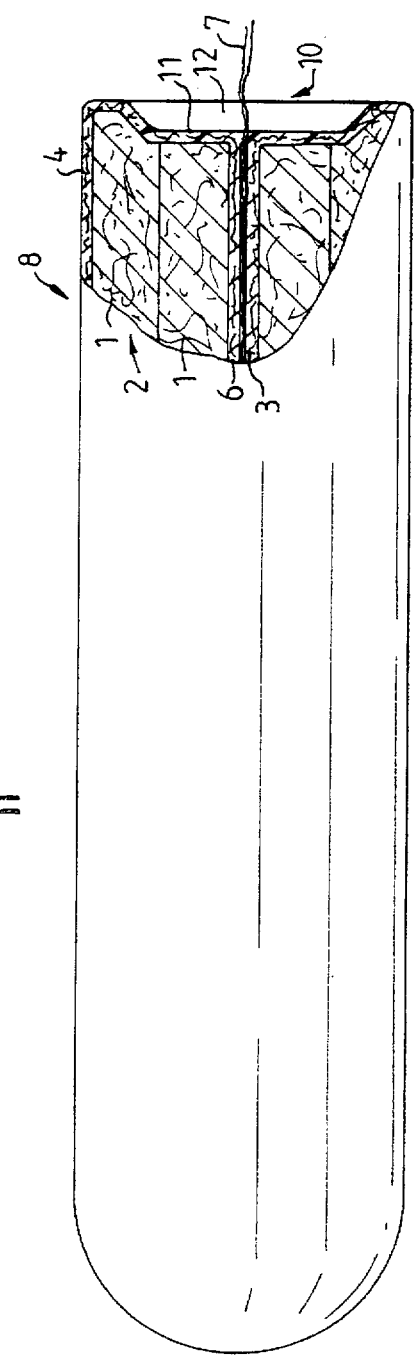

MENSTRUATION TAMPON AND A METHOD OF MANUFACTURING THE SAME

BACKGROUND OF THE INVENTION

The present invention relates to a menstruation tampon.

A tampon of this kind is known, for instance, from British Patent Specification 2,010,680. The absorbent body of this known tampon is formed from a helically wound web of absorbent material and has a central channel which passes axially through the body. The tampon includes an embracing soft casing of non-woven material, which prevents fluff from loosening from the absorbent material of the tampon and remaining in the vagina of the wearer as the tampon is removed after use. The casing material is also folded in and covers the through-passing channel in the centre of the tampon, at least partially. The withdrawal string is able to extend freely from the tampon through said channel, without needing to provide a separate opening in the casing material to this end.

The object of the present invention is to provide an improved tampon of the aforedescribed kind which is more effective in preventing body fluid from leaking from the tampon.

Another object of the invention is to provide a tampon of improved stability. It is also desired to prevent the string end of the tampon from being widened or from swelling as the tampon absorbs body fluid, so that the used tampon will have a form which facilitates its removal. Another object of the invention is to provide a tampon in which the casing is attached to the absorbent body more securely. Naturally, the tampon shall be as comfortable as possible when used.

OBJECTS AND SUMMARY

According to the present invention, these objects are achieved with a tampon of the kind described in the introduction in which the casing includes a thermoplastic material at least at the string end of the tampon, and in which the casing on the surface of said end is heat-sealed to a generally fluid-impervious state, at least in the central parts of said end surface.

The invention also relates to a method of manufacturing such a tampon. Heat-sealing is effected preferably with the aid of a hot mandrel or some like device and by pressing the end surface of the encased tampon against the mandrel and holding the mandrel and said end surface in pressure contact with one another until the thermoplastic casing material has coalesced to an essentially liquid-impervious state, and thereafter separating the tampon from the mandrel.

The coalesced casing material forms a more or less fluid-impervious, leakage-preventing region at the string end of the tampon. It is not necessary to achieve a completely fluid-impervious state, although effectiveness against leakage will increase with increasing imperviousness. The coalesced casing material will also stabilize the end of the tampon and prevent said end from swelling when the tampon absorbs body fluid.

Maximum softness is retained in the outer cylindrical surface, or mantle surface, of the tampon, when the heat-sealed region of said end surface does not extend out to the mantle surface. However, the heat-sealed region may be extended over the whole of the end surface and optionally slightly along the mantle surface, without causing discomfort to the wearer. This improves security against fluid leakage still further and also greatly increases the stability of the string end of the tampon, thereby facilitating insertion and removal of the tampon.

The thermoplastic material in the tampon casing is preferably a non-woven material. The use of other materials, such as perforated plastic film or a thermoplastic net is also conceivable. Suitable materials include all heat-meltable plastics, such as polyethylene and polypropylene. The plastics may be present in mixtures or in the form of bicomponent fibres. The entire tampon casing is preferably comprised of one and the same material, which facilitates manufacture.

BRIEF DESCRIPTION OF THE DRAWINGS

An exemplifying embodiment of the invention will now be described in more detail with reference to the accompanying drawing, in which FIG. 1 is a schematic, sectional view of a known tampon during a stage of its manufacture; and FIG. 2 is a side view, partially in axial section, of an inventive tampon.

DETAILED DESCRIPTION OF PREFERRED EMBODIMENTS

A rectangular web 1 of absorbent material is wound spirally in a number of turns, of which two are shown in the Figure. The web turns form a cylindrical absorbent body 2 which has a central channel 3 passing axially therethrough. The absorbent material may be of any suitable known kind, for instance fibre wadding produced from absorbent cellulose fibres, such as rayon or cotton. The absorbent body may also include a small quantity of thermoplastic binding fibres or the like, to stabilize the finished tampon.

A casing 4 of non-woven thermoplastic fabric is placed over the whole of the mantle surface of the absorbent body 2. The axial length of the casing 4 is greater than the axial length of the absorbent body 2 and the projecting end parts 5 and 6 of the casing 4 are folded into the central channel 3. A withdrawal string 7 is secured to the absorbent body, by placing the string in a loop around one of the winding turns 1. The ends of the string 7 are exited from the absorbent body 2, through its central channel 3.

The tampon blank illustrated in FIG. 1 is then compressed or compacted, primarily radially, to form a tampon rod. FIG. 2 illustrates one such tampon rod 8 from one side of the rod and with part of the outer casing removed. Also shown schematically in FIG. 2 is a heated mandrel 9 which is positioned opposite the string end 10 of the tampon 8. The mandrel 9 can be moved axially towards and away from the string end 10, as indicated by the double-headed arrow P. When the tampon blank shown in FIG. 1 has been compressed to its final shape, the mandrel 9 is pressed against the end surface 10. The mandrel 9 is heated to a temperature which is so chosen in relation to the thermoplastic material in the casing 4 as to cause said material to melt when coming into contact with the mandrel 9 and therewith form a generally liquid-impervious plastic film 11 on the end surface 10 of the tampon 8. Subsequent to having formed the plastic film 11, the mandrel is withdrawn from contact with the end surface 10. As shown in FIG. 2, the mandrel 9 forms a shallow recess 12 in the end surface 10. The end of the tampon is now impervious to fluid within the entire area over which the plastic film 11 has melted, therewith preventing leakage. As the casing material melts and later solidifies, adjacent fibres in the absorbent body 2 are bound together, thereby stabilizing the tampon in this region and anchoring the casing 4 to the absorbent body 2.

In the embodiment illustrated in FIG. 2, the diameter of the mandrel 9 is smaller than the diameter of the end surface 10 of the tampon. Alternatively, the whole of the end surface may be heat-sealed with the aid of a heated plate or the like instead of using the mandrel 9, thereby obtaining improved protection against leakage. Furthermore, it is possible to heat-seal the casing material also on the mantle surface of the tampon adjacent the end surface 10, with the aid of appropriate means. In addition to obtaining improved protection against leakage, this will also further stabilize the end of the tampon so as to prevent the tampon from expanding as it absorbs body fluid.

In the aforegoing, it has been said that the mandrel 9 is moved towards and away from the end surface 10 of the tampon. However, if found suitable from the aspect of manufacture, the mandrel 9 may, of course, be stationary and the tampon movable.

I claim:

1. A menstruation tampon comprising:

a generally cylindrical, fibrous absorbent body;

a withdrawal string which is connected to the tampon and which exits from the tampon at a first tampon end thereof;

a liquid-permeable casing which comprises thermoplastic material and encloses the absorbent body;

the absorbent body having an axial end surface at said first tampon end;

the casing at the first tampon end is in contact with said axial end surface of the absorbent body;

the casing having been heat treated at a heat treated region to melt the casing material in said heat treated region to form an essentially liquid-impervious film at least over a central part of said axial end surface; and fibres of the absorbent body are bonded to the casing within the heat treated region of the casing.

2. A tampon according to claim 1, wherein the heat treated region has a smaller diameter than said first tampon end.

3. A tampon according to claim 1, wherein the absorbent body has a cylindrical surface and the thermoplastic casing material extends up over the cylindrical surface and is also heat treated within the part of the cylindrical surface located adjacent said first tampon end.

4. A tampon according to claim 1, wherein the absorbent body includes at least one web of absorbent material which is wound essentially spirally and has a central, axially through-passing channel and in that the withdrawal string exits through said channel.

5. A tampon according to claim 1, wherein the casing is comprised of thermoplastic non-woven fabric.

6. A tampon according to claim 1, wherein the casing is comprised of perforated plastic film.

7. A tampon according to claim 1, wherein the casing is comprised of a net of thermoplastic material.

8. A method of producing a menstruation tampon comprising a generally cylindrical, fibrous absorbent body, a withdrawal string which is connected to the tampon and which exits from the tampon at a first tampon end thereof, and a liquid-permeable casing which comprises thermoplastic material and encloses the absorbent body and which is heat treated at a central part of said first tampon end; and the absorbent body having an axial end surface at said first tampon end, comprising the steps of:

compressing the absorbent body enclosed by the casing, after the compression, heat treating the casing at a heat treated region to melt the casing material in said region to form an essentially liquid-impervious film over at least a central part of said axial end surface, and bonding fibres of the absorbent body to the casing within the heat treated region of the casing.

9. A method according to claim 8, further comprising the step of performing said heat treatment with the aid of a heating body, by pressing together the heating body and said first tampon end and maintaining said heating body and said first tampon end in pressure contact with one another until the thermoplastic casing material has coalesced to an essentially liquid-impervious state, and then separating the heating body from said first tampon end.

10. A method according to claim 8, further comprising the steps of heat treating the casing material on the tampon cylindrical surface adjacent said first tampon end to render it essentially fluid-impervious.

11. A tampon according to claim 1, wherein the absorbent body includes a small quantity of thermoplastic binding fibers to stabilize the tampon at least at said first tampon end.

12. A tampon according to claim 1, wherein the withdrawal string is secured to the absorbent body.

13. A method according to claim 9, wherein the heating body is a hot mandrel.

* * * * *